(12) United States Patent
Maspero et al.

(10) Patent No.: US 8,163,030 B2
(45) Date of Patent: Apr. 24, 2012

(54) BIOCOMPATIBLE BONE IMPLANT COMPOSITIONS AND METHODS FOR REPAIRING A BONE DEFECT

(75) Inventors: Fabrizio Alessandro Maspero, Duillier (CH); Kurt Ruffieux, Thalwil (CH)

(73) Assignee: Degradable Solutions AG, Schlieren (CH)

( * ) Notice: Subject to any disclaimer, the term of this patent is extended or adjusted under 35 U.S.C. 154(b) by 968 days.

(21) Appl. No.: 10/840,041

(22) Filed: May 6, 2004

(65) Prior Publication Data

US 2005/0251266 A1  Nov. 10, 2005

(51) Int. Cl.
*A61F 2/28* (2006.01)
(52) U.S. Cl. .................................... 623/23.51
(58) Field of Classification Search ............... 623/16.11, 623/23.51, 23.58, 23.61, 23.62; 424/422, 424/423, 426; 523/115, 116; 423/308, 311
See application file for complete search history.

(56) References Cited

U.S. PATENT DOCUMENTS

| | | | |
|---|---|---|---|
| 3,918,968 A | 11/1975 | Freeman et al. | |
| 3,919,773 A | 11/1975 | Freeman et al. | |
| 4,237,559 A | 12/1980 | Borom | |
| 4,429,691 A | 2/1984 | Niwa et al. | |
| 4,430,760 A * | 2/1984 | Smestad | 623/10 |
| 4,610,692 A | 9/1986 | Eitenmuller et al. | |
| 4,645,503 A | 2/1987 | Lin et al. | |
| 4,685,883 A | 8/1987 | Jernberg | |
| 4,938,763 A | 7/1990 | Dunn et al. | |
| 5,077,049 A | 12/1991 | Dunn et al. | |
| 5,278,201 A | 1/1994 | Dunn et al. | |
| 5,324,520 A | 6/1994 | Dunn et al. | |
| 5,338,772 A | 8/1994 | Bauer et al. | |
| 5,340,849 A | 8/1994 | Dunn et al. | |
| 5,433,751 A | 7/1995 | Christel et al. | |
| 5,487,897 A | 1/1996 | Polson et al. | |

(Continued)

FOREIGN PATENT DOCUMENTS

DE       3106445 A1    11/1982

(Continued)

OTHER PUBLICATIONS

Robert C. Thomson et al., *Hydroxyapatite fiber reinforced poly(alpha-hydroxyester) foams for bone regeneration*, Biomaterials, Elsevier Science Publishers BV., Barking, GB, vol. 19, No. 21, Nov. 1998, pp. 1935-1943.

(Continued)

*Primary Examiner* — Anu Ramana
(74) *Attorney, Agent, or Firm* — Buchanan Ingersoll & Rooney PC

(57) ABSTRACT

Moldable bone implants for use in a bone defect or wound include a plurality of biocompatible granules and a biocompatible polymer that together form an implant mass. The polymer is softened with a plasticizer to make the implant mass moldable. The plasticizer can dissipate or be extracted to cause the implant mass to harden. The implant mass can be shaped in-situ or ex-situ. Implants formed in-situ are shaped by the bone defect or wound. The implant becomes hard through contact with body fluids, which extracts the plasticizer from the implant mass. Bone implants formed ex-situ, such as in a mold, are shaped by a mold, for example, and then hardened by placing the implant mass in contact with a hardening agent, such as water, which extracts the plasticizer from the implant mass. The shaped, hardened implant can be placed into a bone defect of corresponding size and shape.

38 Claims, 5 Drawing Sheets

U.S. PATENT DOCUMENTS

| | | | |
|---|---|---|---|
| 5,501,687 A | | 3/1996 | Willert et al. |
| 5,531,791 A | * | 7/1996 | Wolfinbarger, Jr. ......... 623/23.63 |
| 5,552,454 A | | 9/1996 | Kretschmann et al. |
| 5,626,861 A | * | 5/1997 | Laurencin et al. ............ 424/426 |
| 5,648,097 A | | 7/1997 | Nuwayser |
| 5,681,873 A | | 10/1997 | Norton et al. |
| 5,702,716 A | * | 12/1997 | Dunn et al. ................... 424/422 |
| 5,725,491 A | | 3/1998 | Tipton et al. |
| 5,733,950 A | | 3/1998 | Dunn et al. |
| 5,741,329 A | | 4/1998 | Agrawal et al. |
| 5,866,155 A | | 2/1999 | Laurencin et al. |
| 5,962,006 A | | 10/1999 | Southard et al. |
| 6,120,789 A | | 9/2000 | Dunn |
| 6,132,214 A | | 10/2000 | Suhonen et al. |
| 6,143,314 A | | 11/2000 | Chandrashekar et al. |
| 6,201,039 B1 | * | 3/2001 | Brown et al. ................. 523/115 |
| 6,203,574 B1 | | 3/2001 | Kawamura |
| 6,261,583 B1 | | 7/2001 | Dunn et al. |
| 6,294,187 B1 | * | 9/2001 | Boyce et al. ................. 424/422 |
| 6,332,779 B1 | * | 12/2001 | Boyce et al. ................. 433/215 |
| 6,340,477 B1 | * | 1/2002 | Anderson ..................... 424/488 |
| 6,344,496 B1 | * | 2/2002 | Niederauer et al. .......... 523/113 |
| 6,432,438 B1 | | 8/2002 | Shukla |
| 6,455,024 B1 | | 9/2002 | Glajch et al. |
| 6,461,631 B1 | | 10/2002 | Dunn et al. |
| 6,616,698 B2 | * | 9/2003 | Scarborough .............. 623/23.51 |
| 6,696,073 B2 | * | 2/2004 | Boyce et al. ................. 424/422 |
| 6,770,695 B2 | * | 8/2004 | Ricci et al. ................... 524/423 |
| 6,869,445 B1 | | 3/2005 | Johnson |
| 7,001,551 B2 | * | 2/2006 | Meredith ...................... 264/101 |
| 7,241,316 B2 | * | 7/2007 | Evans et al. ................ 623/23.51 |
| 7,270,813 B2 | * | 9/2007 | Shimp et al. ................. 424/93.7 |
| 7,731,756 B2 | | 6/2010 | Maspero et al. |
| 2001/0014831 A1 | | 8/2001 | Scarborough |
| 2002/0016636 A1 | | 2/2002 | Ricci et al. |
| 2002/0028511 A1 | * | 3/2002 | de Bruijn et al. ............. 435/395 |
| 2003/0009235 A1 | | 1/2003 | Manrique et al. |
| 2003/0026770 A1 | | 2/2003 | Szymaitis |
| 2003/0055512 A1 | | 3/2003 | Genin |
| 2003/0104029 A1 | | 6/2003 | Pirhonen et al. |
| 2005/0209704 A1 | | 9/2005 | Maspero et al. |
| 2005/0249773 A1 | | 11/2005 | Maspero et al. |
| 2006/0136071 A1 | | 6/2006 | Maspero et al. |

FOREIGN PATENT DOCUMENTS

| | | |
|---|---|---|
| DE | 3134728 A1 | 3/1983 |
| EP | 0 950 403 A2 | 10/1999 |
| EP | 1344538 | 9/2003 |
| WO | WO 87/05521 | 9/1987 |
| WO | WO 90/01342 | 2/1990 |
| WO | WO 92/00718 | 1/1992 |
| WO | WO 95/27481 | 10/1995 |
| WO | WO 95/28124 | 10/1995 |
| WO | WO 96/21427 | 7/1996 |
| WO | WO 00/01760 | 1/2000 |
| WO | WO 00/06117 | 2/2000 |
| WO | WO 00/35510 | 6/2000 |
| WO | WO 00/50104 A1 | 8/2000 |
| WO | WO 03/004764 A1 | 1/2003 |
| WO | WO 03/047646 | 6/2003 |

OTHER PUBLICATIONS

D J Mooney et al., *Novel approach to fabricate porous sponges of poly(d, l-lactic-co-glycolic acid) without the use of organic solvents*, Biomaterials, Elsevier Science Publishers BV., Barking, GB, vol. 17, No. 14, Jul. 1996, pp. 1417-1422.

Robert C. Thomson et al., "Hydroxyapatite fiber reinforced poly($\alpha$-hydroxy ester) foams for bone regeneration", Biomaterials, Elsevier Science Publishers BV, Barking, GB, vol. 19, No. 21, Nov. 1998, pp. 1935-1943.

David J. Mooney et al., "Novel approach to fabricate porous sponges of poly(D,L-lactic-co-glycolic acid) without the use of organic solvents", Biomaterials, Elsevier Science Publishers BV, Barking, GB, vol. 17, No. 14, Jul. 1996, pp. 1417-1422.

Definition of "Conditioner" (http://www.thefreedictionary.com/conditioner), citing The American Heritage Dictionary of the English Language, Fourth Edition, 2000, Houghton Mifflin Company, Updated 2009.

H. H. Lu, *3-D Porous Polymer-Bioactive Glass Composite Promotes Collagen Synthesis and Mineralization of Human Osteoblast-like Cells*, Sixth World Biomaterials Congress Transactions 2000 Society for Biomaterials, p. 972.

Maspero et al., Copending U.S. Appl. No. 11/121,831, filed May 4, 2004, entitled, "Biocompatible Bone Implant Compositions and Methods for Repairing a Bone Defect".

Maspero et al., Copending U.S. Appl. No. 10/507,094, filed Sep. 3, 2004, entitled, "Porous Biocompatible Implant Material and Method for Its Fabrication".

* cited by examiner

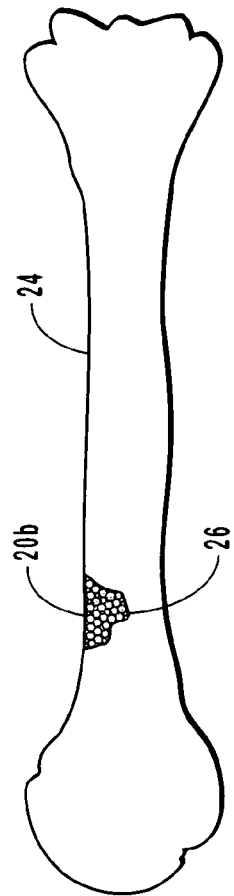
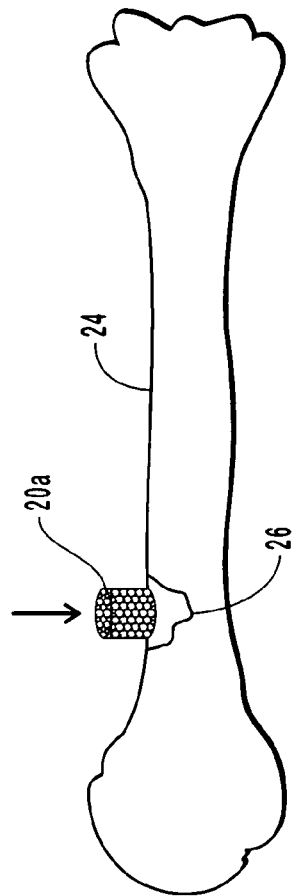
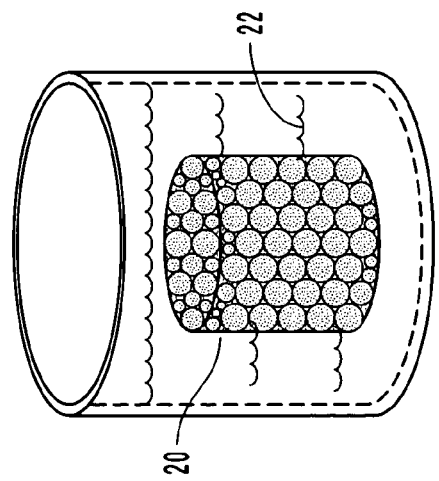
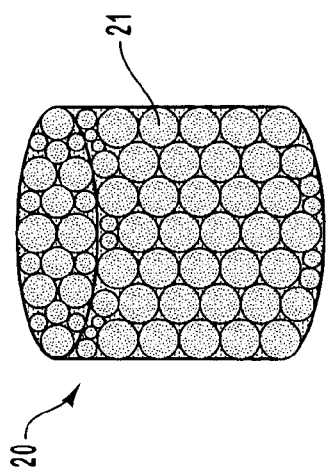

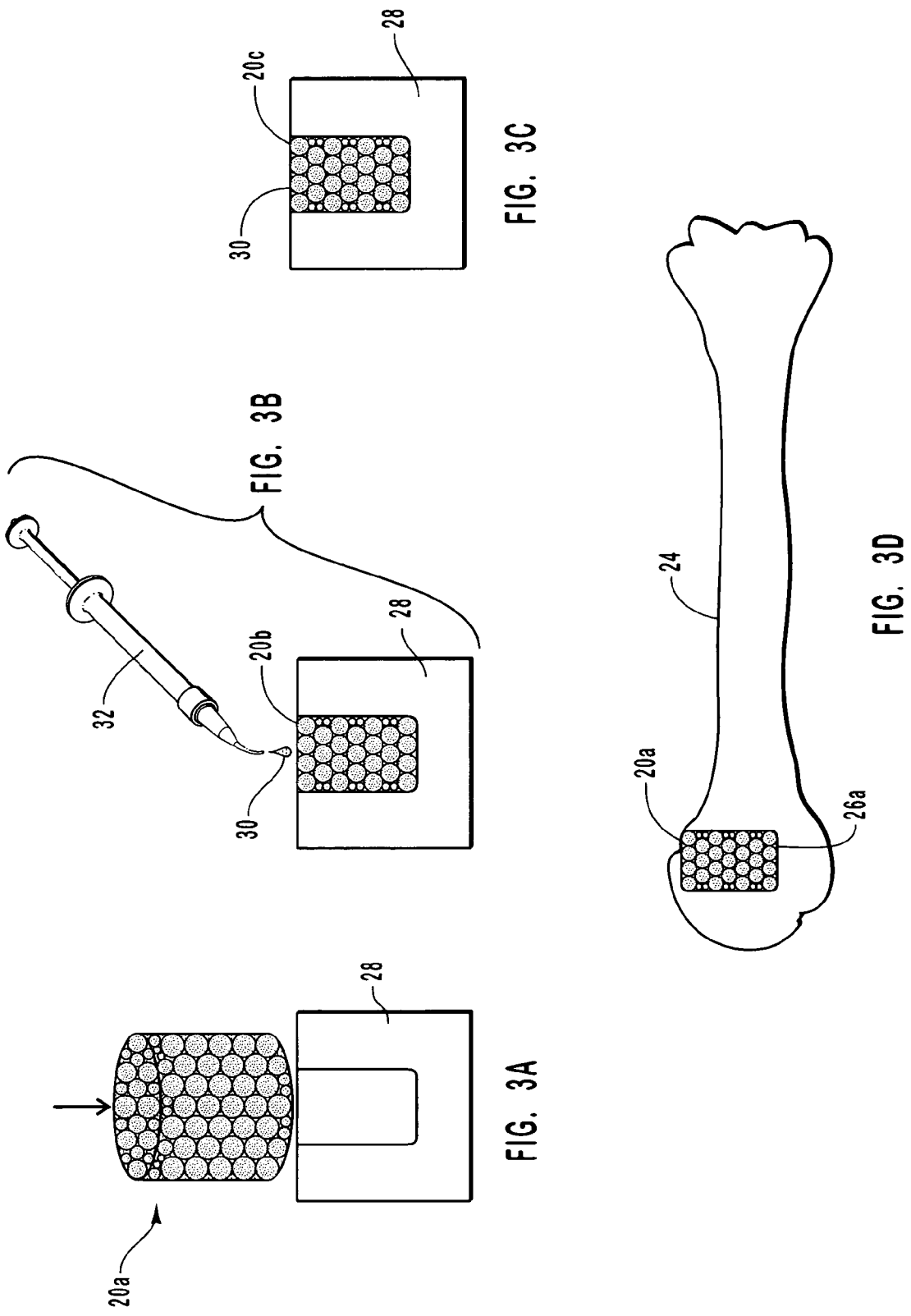

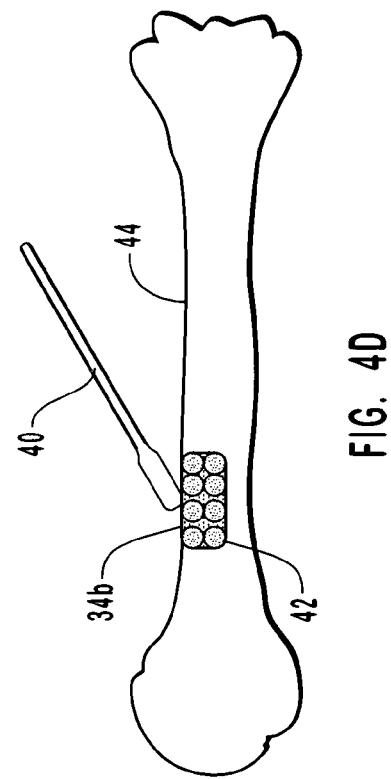
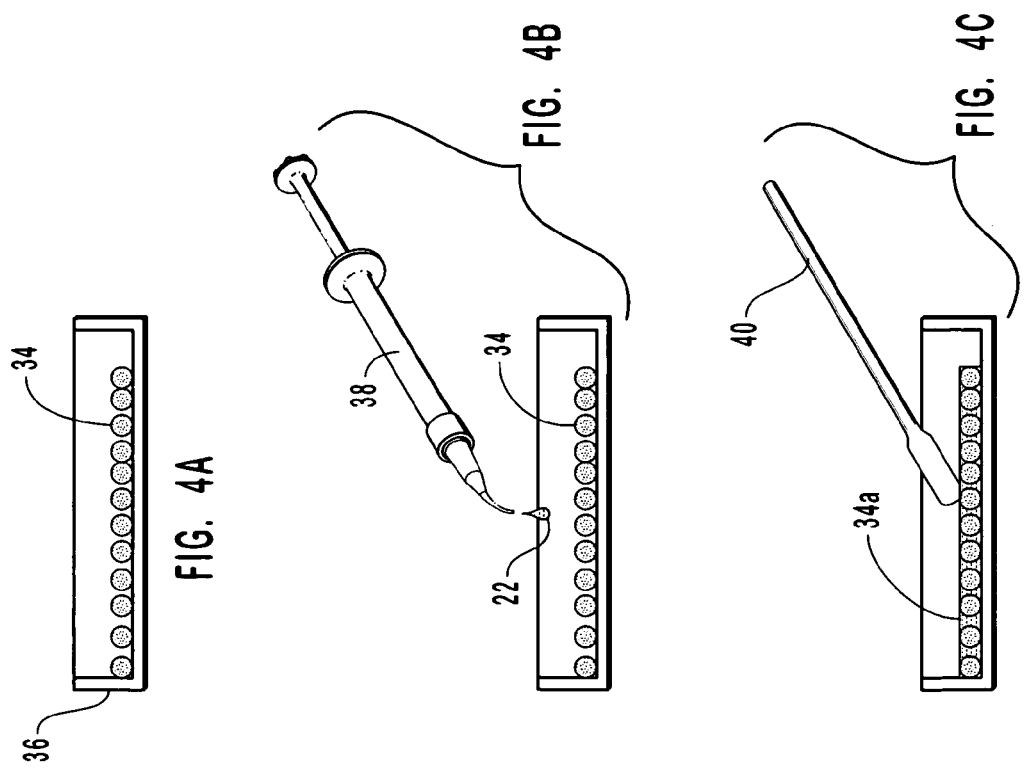

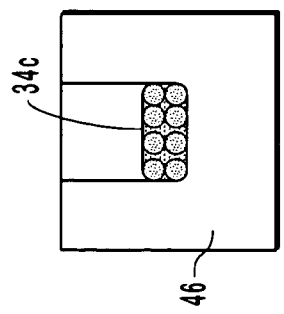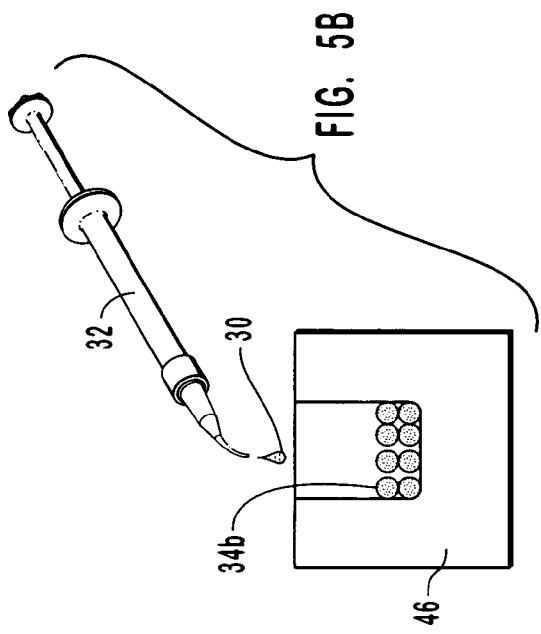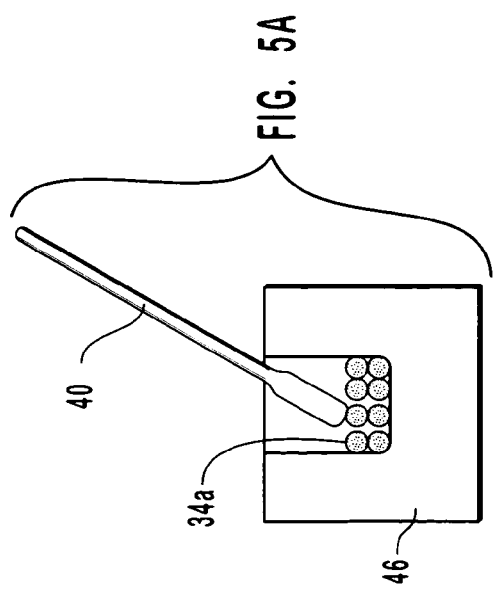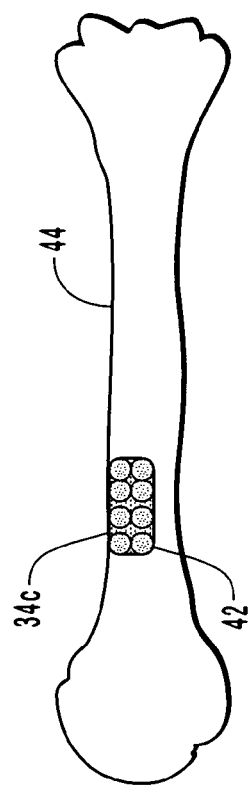

BIOCOMPATIBLE BONE IMPLANT COMPOSITIONS AND METHODS FOR REPAIRING A BONE DEFECT

BACKGROUND OF THE INVENTION

1. The Field of the Invention

The present invention is related to biocompatible implants for treating defects in living organisms, such as bone defects and tooth extraction wounds. More specifically, the present invention relates to moldable biocompatible implants.

2. Related Technology

The importance of bone replacement materials, in particular in the areas of orthopedics, traumatology, cranial, dental and facial surgery, and orthodontics continues to increase. Significant areas of application for bone implants include, for example, the closing of large bone defects associated with comminuted fractures as well as the attachment of small bone fragments, the filling of bone defects resulting from bone cysts and after removal of bone tumors, the filling of voids caused by chronic osteomyelitis, applications associated with material loss on alveolis and jaw bones and the use as a carrier material, for example, for antibiotics, cytostatic, and osteogenic materials.

In most cases, bone defects can be treated by the insertion of bone augmentation materials. Healing is promoted if the implants closely contact the surrounding bone walls. Thus, it is advantageous to be able to form a bone implant in a particular shape. For instance, if a tooth is extracted, the bone implant used to fill the void preferably nearly replicates the tooth root. Improperly shaped bone implants can lead to problems such as soft tissue ingrowth and poor adhesion between the implant and existing bone. In addition, improper shape can lead to complications or patient discomfort.

Properly shaping a bone implant is often very challenging. In some cases the repair site is deep within the body and covered by soft tissue and body fluids. In other cases, such as with a tooth extraction, the root of the extracted tooth can be used to make a mold. However, even when repairing a tooth extraction wound, there are times when the root is broken into pieces and not available for molding. In other situations, the bone implant must be molded after it has been placed in the injury site. Most existing bone implant materials, however, require steps, such as heating, that prevent forming the implant in-vivo.

One type of existing implant uses calcium phosphate or bioglass granules to fill and treat bone defects. These granular-type implants are biodegradable and osteoconductive. While existing granular bone implants can promote bone tissue in-growth, the formation and retention of these implants can be complex. In some cases, a membrane is required to maintain the granules at the implantation site.

Another type of implant system uses injectable materials such as a polymer solution or a dispersion of microparticles. The injectable systems improve handling and moldability. However, injectable systems are typically non-biodegradable and prevent new bone formation throughout the implant (i.e. they have low osteoconduction). For example a known injectable material such as polymethylmethacrylate (PMMA) is non-biodegradable and inhibits natural bone from forming in the bone defect. Calcium phosphate cements can be biodegradable, but often lead to the formation of dense or solid or may contain small closed pores implants that inhibit osteoconduction.

One recent bone implant that improves upon the injectable polymer implants uses a solid polymeric material that is soaked in an organic solvent such as N-methyl-2-pyrrolidone (NMP) to soften the implant. The implant can then be molded to a desired shape in-situ. This implant, however, is also solid and non-porous or may contain small pores. The natural bone surrounding the implant cannot integrate into this implant nor replace it with regenerative bone tissue, unless the implant is degraded. Unlike an osteoinductive and/or osteoconductive implant, these implants have limited use for restoring the wound or defect to a more natural condition (i.e., they fill rather than heal the defect).

In another attempt to improve bone implants, a defect analog or mold is made from a piece of extracted bone, such as an extracted tooth root. The mold can then be used to make a porous and biodegradable replica. One disadvantage of using a defect analog is that it requires the integrity of a tooth root or other piece of bone to make the mold. In addition, the implant manufacturing process often requires a small heating device or a $CO_2$ autoclave, thus increasing the expense and complexity of the process. Even where shaping the implant in a mold is desired, there is a need to simplify the process for shaping regenerative bone implants such that the implants can be shaped in a more timely fashion.

Therefore, what is needed is a biodegradable implant that can be easily and quickly shaped in-situ or ex-situ into a desired form and that can promote the in-growth and regeneration of bone tissue.

BRIEF SUMMARY OF THE INVENTION

Exemplary embodiments of the present invention overcome the above-mentioned problems in the prior art by providing an osteoconductive and/or osteoinductive biocompatible implant composition that that can be readily molded in-situ or ex-situ into a desired shape. In an exemplary embodiment, once the moldable implant composition is formed into a desired shape, the implant composition is easily, and if desired, quickly hardened to form a rigid implant. In one embodiment, an implant composition according to the invention forms an open porous scaffolding or composite matrix that allows in-growth and/or regeneration of bone tissue.

In an exemplary embodiment, the moldable implant composition of the present invention includes a plurality of biocompatible granules mixed with a biocompatible polymer and a plasticizer for the polymer. The biocompatible polymer and the biocompatible granules form an implant mass for use in a bone defect of a living organism. The plasticizer is included in an amount sufficient to condition at least a portion of the biocompatible polymer such that the implant mass can be molded (i.e., is plastically deformable). The implant mass can be inserted in a bone defect where the implant mass can be deformed so as to assume the shape of the defect. The moldable implant composition can be deformed, molded, and/or sculpted to have any particular shape, either in-situ or ex-situ.

In one embodiment of the invention, the plasticizer is selected to cooperate with a hardening agent. Once the hardening agent is applied to the bone implant composition, the effect of the plasticizer is neutralized and the bone implant composition hardens, thereby providing proper structural support. In an exemplary embodiment, the plasticizer is partially soluble in an aqueous solution such as a body fluid such that the body fluid can act as a hardening agent by extracting at least a portion of the plasticizer from the implant composition.

The ability to selectively mold and harden the bone implant composition of the present invention provides a surgeon with the option to more easily and more quickly repair a bone defect. Because the implant mass or composition can be shaped in-situ, a surgeon can quickly and accurately fill a void without first having to form a mold. While the softened bone implant mass is moldable, it is not so soft that it can flow like a liquid (i.e., it is not a fluid but plastically deformable). The firmness of the moldable bone implant composition allows the implant composition to maintain a desired shape until the hardener causes it to solidify. The ability to maintain a desired shape even while moldable alleviates some of the need to have the implant composition harden immediately and allows the implant of the present invention to be used in-situ where lower volumes of body fluid are present and where irrigation with a fluid such as water is not possible.

The moldable implant compositions may also be shaped ex situ using a mold. The moldable implant composition of the present invention can easily deform to the shape of the mold and then be quickly hardened using a hardening agent. Shaping and hardening the implant composition in a mold according to methods of the present invention can save valuable time during a surgical operation thereby reducing costs and risks. In addition, a practitioner may decide during an operation that an implant needs to be molded and placed in-situ. For instance, during a tooth extraction a tooth's root may partially break, thereby creating the need to place an implant in-situ, even if the preferred method of forming the implant is using a mold ex situ. The implants of the present invention provide a practitioner with the ability choose the best method for a particular situation.

In another embodiment of the present invention, the plurality of granules are formed from a bone-like (or bone compatible) ceramic such as calcium phosphate or other calcium-based minerals. Implants made with calcium phosphate ceramics according to the present invention exhibit qualities such as the ability to (i) develop direct adhesion and bonding with existing bone tissue; (ii) promote cellular function and expression; (iii) provide a scaffold or template for the formation of new bone; and (iv) promote osteogenesis and act as a carrier for bioactive materials.

These and other features of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 2A illustrates an exemplary pre-formed bone implant composition according to the present invention;

FIG. 2B illustrates the bone implant composition of FIG. 2A being softened by being immersed in a plasticizer liquid;

FIG. 2C illustrates the softened implant composition of FIG. 2B being inserted into a bone defect;

FIG. 2D illustrates the softened implant composition of FIGS. 2B and 2C being molded to the shape of a bone defect in situ;

FIG. 3A is an exemplary method of the present invention illustrating the softened implant composition of FIG. 2B being inserted into a mold;

FIG. 3B illustrates the shaped implant composition of FIG. 3A in the mold and having a hardener added thereto;

FIG. 3C shows the shaped implant composition of FIG. 3B in a hardened state;

FIG. 3D shows the hardened implant composition of FIG. 3C inserted into a bone defect having substantially the same shape;

FIG. 4A illustrates a plurality of granules according to one embodiment of the present invention;

FIG. 4B illustrates a plasticizer being added to the granules of FIG. 4A;

FIG. 4C illustrates the softening of the plasticized granules of FIG. 4B;

FIG. 4D illustrates the shaping of a bone implant in a bone using the softened granules of FIG. 4C;

FIG. 5A is an exemplary embodiment of a method of the present invention using the softened granules of FIG. 4C to make an implant mass shaped in a mold;

FIG. 5B illustrates the hardening of the shaped implant mass of FIG. 5A using a hardener;

FIG. 5C illustrates the implant composition of FIG. 5B in a hardened state; and

FIG. 5D illustrates the hardened implant composition of FIG. 5C inserted into a bone defect.

DETAILED DESCRIPTION OF EXEMPLARY EMBODIMENTS

Embodiments of the present invention include moldable bone implant compositions for repairing a bone defect or wound. The moldable implant compositions are formed from a plurality of particle-like granules. A biocompatible polymer is disposed about or coated on the granules. The granules and polymer are packed or agglomerated to form an implant mass and the polymer is softened with a plasticizer to make the implant mass moldable. The implant mass is shaped or sculpted to form a bone implant that will fill a particular bone defect or structural void. The bone implant is then allowed or caused to harden. As discussed more fully below, the order and timing of (i) softening the polymer, (ii) forming the implant mass, and (iii) shaping the implant mass can vary according to different embodiments of the present invention.

Figure 1B:
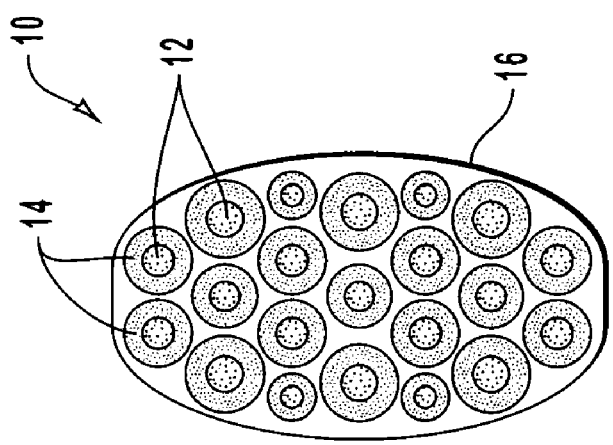
FIG. 1B is a cross-sectional view of the moldable implant composition of FIG. 1A.
Figure 1A:
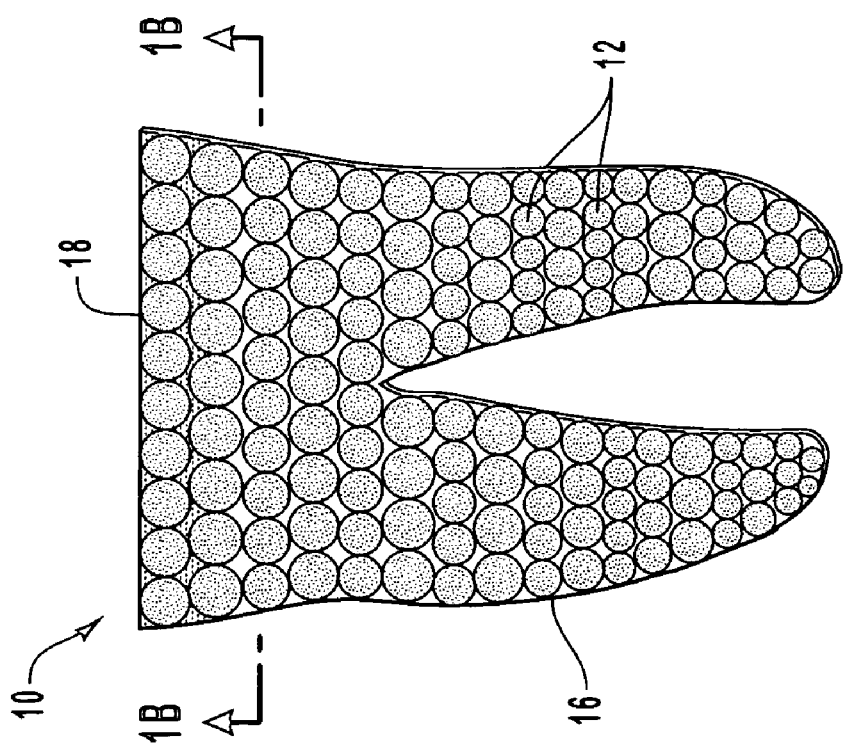
FIG. 1A illustrates an exemplary moldable implant composition shaped like a tooth root according to the present invention.

Turning now to FIGS. 1A and 1B, the present invention includes a moldable bone implant composition 10 for repairing a bone defect or wound. In an exemplary embodiment, the moldable implant composition 10 includes a plurality of granules 12. The granules are coated with a biocompatible polymer 14 (FIG. 1B) and are packed together to form an implant mass 16. The implant mass 16 further includes a plasticizer included in, or mixed with at least a portion of, the biocompatible polymer. The plasticizer softens the biocompatible polymer 14, which allows the moldable implant composition 10 to be molded into a desired shape. As illustrated, the moldable implant composition 10 has the shape of a root from placing the moldable implant in a mold or from inserting the implant into the extraction site. It will be appreciated that the implant composition can assume the shape of any bone defect. The moldable implant composition is preferably "plastically deformable" (i.e., will maintain whatever shape it is molded into prior to hardening absent application of a further shaping force).

In an exemplary embodiment, the moldable implant composition 10 has an implant mass 16 that forms a composite matrix. Implant mass 16 has macro-pores that are formed throughout the matrix of biocompatible granules 12 and biocompatible polymer 14. The implant mass 16 can also have micro-pores formed in biocompatible polymer 14 or granules 12. In one embodiment, moldable implant 10 has a membrane 18 formed thereon, which inhibits soft tissue in-growth.

I. Components of the Bone Implant Composition

The various components of an implant according the present invention will now be discussed. The headings used herein are intended to make the disclosure easier to understand and should not be considered limiting in any way.

a. Granules

In an exemplary embodiment, the present invention includes biocompatible granules, which are a hard substance that provides structural support or physiological advantages to the implant mass. The granules can be made of synthetic, naturally occurring, polymeric, or non-polymeric materials. In one embodiment, the granules are also biodegradable such that the implant degrades over time and/or be replaced with native bone tissue.

The biocompatible granules of the present invention can be made of a synthetic, biocompatible material, such as biopolymers, bioglasses, bioceramics, more preferably calcium sulfate, silicon oxide, calcium phosphate such as, for example, monocalcium phosphate monohydrate, monocalcium phosphate anhydrous, dicalcium phosphate dihydrate, dicalcium phosphate anhydrous, tetracalcium phosphate, calcium orthophosphate phosphate, calcium pyrophosphate, α-tricalcium phosphate, β-tricalcium phosphate (β-TCP), apatite such as hydroxyapatite (HA), or polymers such as, for example, poly(α-hydroxyesters), poly(ortho esters), poly (ether esters), polyanhydrides, poly(phosphazenes), poly (propylene fumarates), poly(ester amides), poly(ethylene fumates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or co-polymers, terpolymers thereof or blends of those polymers, or a combination of biocompatible and biodegradable materials.

The following materials can also be used as a structural component in the present invention and are considered to be synthetic materials: Chitin and chitosan, which may be derived form tissues of marine non-vertebrate animals; hyaluronic acid, a polysaccharide, which can be obtained from a rooster comb or by micro-organism fermentation; poly (amino acids) and polypeptides, which may be produced by biotechnological processes; any polysaccharide, which is obtained from plants, from non-vertebrate animals or by biotechnological processes (e.g. alginate).

Calcium phosphate ceramics are biocompatible and can be used in various biomedical applications. HA and β-TCP bioceramics are particularly useful materials because they have similar ionic properties as the mineral components of bone. In addition, their resorption kinetics can be controlled to meet the needs of a specific therapy. Furthermore, because β-TCP is biodegradable, it is absorbed in vivo and can be replaced with new bone growth.

The granules of the present invention can also be made from naturally occurring materials such as ground bone particles or granules formed from, e.g., human, porcine, or bovine bone. The base particles may optionally be partially or wholly demineralized, or the organic components can be partially or wholly removed.

In an exemplary embodiment, biocompatible and/or biodegradable granules are selected, which have an equivalent-diameter of about 100 μm to about 4000 μm, and preferably from about 500 μm to about 1500 μm. Granules of the selected equivalent diameters are easily handled and readily further processed.

While the term equivalent-diameter indicates that the synthetic biocompatible and biodegradable granules may be of irregular shape, it can be advantageous to use granules of regular shape, such as spherical granules. In some applications, spherical granules allow a better handling and an easier estimation of the quantity required to fill a known volume of a cavity. Moreover, spherical or other regularly-shaped and/or sized granules form a more uniform pore structure or scaffold between the adjacent particles. Nevertheless, in other applications irregular shaped granules or even granules shaped like rods, chips, and the like, can be advantageous. Furthermore, in some applications, the size of the granules can be sufficiently fine that the granules form microspheres or a powder.

In another embodiment of the invention the granules are porous or hollow. The use of hollow and/or porous granules reduces the amount of implanted materials and allows a better in situ integration. In yet another embodiment, the granules include a macroscopic opening in the granular wall of a hollow granule. The opening in the granule wall promotes tissue in-growth into the matrix of the bone implant.

b. Formation of Granules

In an exemplary embodiment, the granules of the present invention are made from a calcium phosphate ceramic such as β-TCP. Granules made from β-TCP, as discussed above, are advantageous because they are biodegradable and can promote the in-growth and regeneration of natural bone tissue.

To form granules of β-TCP, seventy grams of β-TCP powder (purum p.a. >96%, Fluka, CH) were mixed with 1 g dextrin (Relatin Dextrin K51) in a mortar. Twenty milliliters of deionized water were slowly added to the powdery mixture under continuous stirring. The resultant paste was extruded through a multi-hole (ø:800 μm) nozzle (Cyclo, Typ XYCG, Probst Technik, CH) and spheronized during ca. 3 min in a pelletrounder (Probst Technick, CH) to obtain granules having an average diameter of about 350 μm to about 1000 μm. The obtained β-TCP granules were then calcinated. Other methods such as high-shear mixture and fluidized bed granulation can also be used to produce rounded granules.

Hollow granules with openings in the granule wall can be produced from a slurry of the biocompatible materials, water and an adhesive. Droplets of the slurry are brought onto a heated plate. The water in the slurry droplet boils and evaporates instantaneously out of the droplets leaving an evaporation crate in the droplet wall. When the droplets are cooled off, hollow granules having an opening in the granule wall are formed.

In an alternative embodiment, the granules can be made from a biodegradable polymer such as poly-lactide-co-glycolide (PLGA). To prepare granules of PLGA, a solution of polymer and ethyl acetate (6.25% w/w) was prepared. The solution was introduced dropwise into a stirred PVA solution (0.4% w/w) such that an emulsion was formed. The emulsion was poured into 800 ml of water and stirred for about 5 h. The resulting solution was filtered and the resulting granules dried under vacuum for about 12 hours. The process produced granules having a size ranging from about 40 μm to about 100 μm.

c. Biocompatible Polymer

The bone implant composition of the present invention also includes a biocompatible polymer disposed about the granules to form an implant mass. In one embodiment, a portion of or all of the granules are coated with the biocompatible polymer. In an exemplary embodiment, the biocompatible polymer is also biodegradable so as to promote absorption into the body as the implant is replaced by newly-formed living tissue.

Biocompatible polymers suitable for use in the present invention include poly(α-hydroxyesters), poly(orthoesters), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or co-polymers, terpolymers thereof or blends of those polymers. The polymer can also be selected to be biodegradable.

As explained below, a plasticizer is added to the biocompatible polymer to condition the polymer and make the bone implant moldable. In one embodiment, the biocompatible polymer and the plasticizer are selected to work in a polymer-solvent system. The biocompatible polymer is selected to have a desired flexibility and tackiness when partially dissolved or softened in a particular plasticizer. When the plasticizer is removed (e.g., by evaporation or diffusion into the body), the biocompatible polymer hardens to form a rigid bone implant. The polymer and plasticizer are chosen to give the implant a particular stiffness when softened and hardened.

In order to be easily plastically shaped and/or molded, the bone implant has to be exposed to a temperature higher than the glass transition temperature ($T_g$) of the polymer. In another embodiment, the bone implant can be shaped and/or molded without plasticizer provided the preparation is carried out above $T_g$. In the case of a polymer with $T_g$ higher than the body temperature (37° C.), the bone implant hardens as the temperature decreases if it has been shaped at a temperature higher than 37° C. Thus, in this embodiment, the implant can be heated above $T_g$ to make the implant moldable for implantation in a person or a mold without any plasticizer. In yet another embodiment, the operating temperature can be advantageously reduced by adding a plasticizer. The plasticizer can be a liquid or a gas such as $CO_2$.

d. Preparation of Coated Granules

In an exemplary embodiment, the granules have a biocompatible polymer coated thereon. While the invention will be described herein with reference to coated granules, those skilled in the art will recognize that there are other configurations for mixing granules with polymer.

The synthetic biocompatible, biodegradable granules may be spray-coated, preferably in a fluidized bed machine, or immersion-coated with the desired biocompatible polymer (s). Both methods lead to the biocompatible and biodegradable granules having advantageous properties.

The spray coating process in a fluidized bed machine allows the fabrication of a great number of nearly identical polymer-coated biocompatible and biodegradable granules in a very fast and economic manner. Using the fluidized bed process, allows easy control of the thickness of the coating layer(s) and the fabrication of biocompatible and biodegradable granules having multiple coating layers, which are distinct from each other. The coating in fluidized bed machine results in a homogenous and continuous coating, which offers a barrier against bacterial contamination of the granules or of implants made from them. During the coating process the granules do not adhere to each other, thus avoiding the formation of undesirable aggregates which might lead to highly inhomogeneous size distributions and coating thickness.

Integration of additives such as plasticizers or biologically active substances into the coating(s) can be easily controlled by the fluidized bed machine. Thus, each granule is loaded with the same amount of the biologically active substances. The thickness of the coating is also easily controlled. Therefore, even the release of an integrated biologically active substance is predictable and well controlled.

The coating of the synthetic biocompatible, biodegradable granules may include one or more layers of varying average thickness. At least the outmost coating layer is made of a biodegradable material. This embodiment of the invention allows providing biocompatible and biodegradable granules with several coatings for specific purposes. The outmost biodegradable coating may be selected in accordance with a certain desired delay in degradability. Thus, the coating layer underneath is only exposed after a certain desired time period has expired. This, for example, allows a retarded delivery of a bioactive substance. Thus, the synthetic biocompatible and biodegradable granules may be coated with different coatings, which each is biodegradable and displays a specific effect.

By way of example the invention will be illustrates with reference to polylactide-co-glycolide (PLGA), which is known for its biocompatibility and biodegradability. For this purpose, a solution of PLGA in dichloromethane ($CH_2Cl_2$) is first prepared. The concentration of the polymer was about 0.1 g to 0.2 g PLGA in 1 ml $CH_2Cl_2$. The β-TCP granules are immersed in the PLGA solution. While the resultant mixture is constantly stirred, the solvent evaporates until a thin film of polymer is deposed on the surface of the β-TCP granules. Agglomerated granules can be then separated using a labor mixer and sieved. The extraction of the solvent is finally carried out for 36 h under vacuum (100 mbar). A coating with biologically active substances can also be applied as an individual coating or mixed or dissolved in the polymer coating.

A more economic coating method, which results in a very homogenous coating of the β-TCP granules, is the spray coating process in a fluidized bed machine. This coating process is known to those skilled in the art and has been proven to achieve desired results for homogenous coatings.

The biocompatible polymer coating preferably has a thickness of about 1 µm to about 300 µm, preferably of about 5 µm to about 30 µm. The coating thickness of the granules can also be expressed as a weight fraction of about 4% to about 20% coating materials of the total weight of the implant mass, which may be loaded with additives such as plasticizers or biologically active substances. Those skilled in the art will recognize that by selecting different coating solutions and varying the coating time, different layers of coatings having different thicknesses can be applied to granules.

The mechanical stability of an implant made of coated granules can depend on the thickness and the homogeneity of the coating. An insufficient coating thickness can cause the granules to fail to stick together. On the other hand, too much of a coating can cause a decrease in the pH in the vicinity of the implant during its degradation. Whether the thickness of the coating has an adverse effects on the performance of the implant depends on the particular use of the implant.

e. Biocompatible Plasticizer

The plasticizer is selected to condition the biocompatible polymer. The plasticizer acts as a softening agent or solvent for dissolving or otherwise making the biocompatible polymer moldable and/or sticky. Typically, the plasticizer is added in an amount that will soften the polymer but not liquefy the polymer.

The plasticizer is preferably biocompatible or exhibits a very low toxicity such that it can safely exist in the bone implant once the implant has been placed in a patient. Suitable plasticizers include, but are not limited to, n-methyl-2-pyrrolidone (NMP), acetone, ethyl lactate, ethyl acetate, ethyl formiate, acetyltributylcitrate, triethyl citrate, tetrahydrofuran, toluene, alcohol and carbon dioxide. Those skilled in the art will recognize that the plasticizer of the present invention can be one of many other solvents that condition the biocompatible polymers of the present invention.

In an exemplary embodiment, the plasticizer is a solvent that has solubility in aqueous medium, ranging from miscible to dispersible. Thus, the plasticizer is capable of diffusing into an aqueous medium or into body fluids such as, for example, tissue fluids, such as blood serum, lymph, cerebral spinal fluid, and saliva. When the plasticizer diffuses out of the implant mass, the bone implant is caused to harden. In this way, body fluids can be used as a hardener to solidify the bone implant in-situ.

The bone implant can also be hardened ex-situ by drawing the plasticizer out of the polymer. In one embodiment, the plasticizer is selected to be partially soluble in water. Once the implant is shaped ex-situ, such as in a mold, water is placed on the implant, thereby extracting the plasticizer and hardening the bone implant. Alternatively, the plasticizer can be removed by evaporation (e.g., by heating and/or applying a vacuum).

The solubility or miscibility of the biodegradable polymer in a particular plasticizer may vary according to factors such as crystallinity, hydrophilicity, capacity for hydrogen bonding, and molecular weight. Consequently, the molecular weight and concentration of the biocompatible polymer can be adjusted to modify the plasticizer's solubility. Typically, the polymer-plasticizer system is designed such that the plasticizer softens the polymer but does not liquefy the polymer, thereby creating a sticky, pliable mass.

In one embodiment, the polymer-solvent system is designed to reduce the $T_g$ of the biocompatible polymer to a temperature below room temperature. For example, acetone, NMP, or an alcohol is added to PLGA until the $T_g$ of the PLGA drops from about 50-55° C. to below room temperature. Likewise, PLA and PLGA, which have a $T_g$ of about 43 and 34° C., respectively, can be lowered to below room temperature with the plasticizer.

In another embodiment, the polymer-plasticizer system can be designed to require heating to a temperature above room temperature or an operating temperature. The plasticizer and polymer are selected to lower the $T_g$ to a temperature that is above room temperature but is below a threshold heating temperature. In this way the moldability of the implant can be imparted at certain desired temperature ranges. For instance, the polymer can be made moldable at a temperature that is above a body temperature but low enough that heating the implant until it is moldable does not make the implant too hot to place in a living person.

By adjusting the $T_g$ of the polymer, either with the plasticizer or by changing the composition of the polymer, an implant can be made that is moldable at desired temperatures. Even if heating is required, the $T_g$ of the implant can be made low enough that thermally labile factors such as proteins can be included in the implant without damaging or inactivating the factor.

f. Composite Matrix

According to one embodiment of the present invention, the bone implant has macro-pores and/or micro-pores that form an open porous scaffold or composite matrix. The term "open porous scaffold" or "composite matrix" refers to a structural matrix of granules that are bonded or otherwise joined together so as to define a granular region comprising solid or porous granules and an open porous region comprising spaces or discontinuities between adjacent granules of the granular region. The open porous region may be filled with air or gas at least initially, or it may be at least partially filled with liquid, solid particles, gel, and the like.

The scaffold or composite matrix can be obtained by fusing together granular biomaterial such as polymeric granules and/or coated granules. The scaffold or composite matrix of the biocompatible implant may be made of granules having micropores with average diameters of about larger than 0 to about 10 μm. By the fusion of the granules, the microporosity remains and/or macropores between the granules are formed having average diameters of about more than 10 μm to about 2000 μm, preferably about 100 μm to about 500 μm.

It should be understood that the macropores between the particles comprising the scaffold can simply be void spaces filled with air or gas. It is also within the scope of the invention to at least partially fill some or all of the void spaces with a liquid, gel or solid (e.g., a plurality of particles such as a fine powder). The liquid, gel or solid may include one or more active agents. It is also within the scope of the invention to prepare an implant comprising a shaped composite that includes few, if any, macropores (e.g., by using sufficient polymer between the solid granules so as to fill some or all of the void spaces and create a solid matrix).

The pores of the composite matrix may be filled, e.g., with an antibiotic substance, with growth factors and with similar biologically active substances. Thus, the biocompatible and biodegradable implant, when implanted into a cavity or extraction wound not only fills the cavity but also permits the controlled release of biologically active substances. For example, the substance within the pores may be selected such that bacterial growth is hindered, bone formation is accelerated, or pain at the bone wound is reduced.

By special selection of the biocompatible and biodegradable materials for the synthetic granules and their coatings, the growth and the proliferation of osteoblast-like cells may be supported during the degradation of the implant, which is finally replaced by newly formed bone tissue. The implant may in certain cases also prevent the erosion of the bone tissue surrounding the bone defect to be healed.

It can be advantageous in some cases to provide a biocompatible, biodegradable scaffold or composite matrix, which includes both coated and non-coated granules. The coated and uncoated granules can be thoroughly mixed such that they fuse together and still have the needed stability. By providing a mixture of coated and non-coated granules for the production of the biocompatible and biodegradable implants, the amount of coating materials, which must degrade, may be further reduced.

g. Membrane

The bone implant of the present invention can also include a membrane on an outer surface, which prevents soft tissue in-growth and/or contamination. The biocompatible membrane can be a biodegradable polymer film, polymer textile, polymer fleece or layer of interconnected fused polymer particles or a combination thereof and sealed to the implant, thus forming at least one layer of impermeability to soft tissue and epithelial cells.

In an embodiment of the invention, the membrane is made of a synthetic, biocompatible and biodegradable polymer selected from the group including poly(α-hydroxyesters), poly(ortho esters), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or copolymers, terpolymers thereof or blends of those polymers.

The membrane can also be formed by fusing granules or coated granules together. Granules used for this purpose preferably have a size smaller than about 500 µm and more preferably between about 1 µm to 200 µm.

The fusing of polymer pellets for the creation of the membrane may lead to the formation of pores in the membrane with sizes in the range of 1 µm to 500 µm, preferably of 5 µm to 50 µm. The size of the pores depends on the size of the polymer particles. The size of the particles is so selected such that the membrane may be porous, allowing the transport of fluids, but forming a barrier against soft tissue and/or epithelial cells in-growth into the implant. The porosity can enhance the vascularization of the implant and, thus, promote the healing of the implantation site.

II. Formation of Bone Implant

As mentioned above, formation of the bone implant includes (i) softening the polymers as to form an implant mass that is moldable (i.e., plastically deformable); and (ii) shaping the moldable implant mass into a desired shape (ex situ or in situ). In various embodiments of the present invention, these steps are performed in a different order and/or simultaneously. Unless otherwise specified, the term "unshaped" means an implant mass that needs a substantial amount of molding to reach its final shape in a patient. The term "shaped" means an implant that is sufficiently shaped such that it needs little or no molding to function as an implant in a patient.

FIGS. 2A-2D illustrate an exemplary embodiment of the present invention where an unshaped implant mass 20 is formed and then softened. In FIG. 2A coated granules 21 are packed to form an unshaped implant mass 20. In this embodiment, coated granules 21 are allowed to dry and then agglomerated in an unshaped form. Implant mass 20 has little or no plasticizer such that it is hard. Unshaped implant mass 20 can be easily stored or shipped without affecting the implant's condition.

As shown in FIG. 2B, to use implant mass 20, implant mass 20 is submerged in a liquid plasticizer 22. The biocompatible polymer of implant mass 20 and the plasticizer 22 are selected such that the biocompatible polymer absorbs plasticizer 22. Unshaped implant mass 20 is left in plasticizer 22 until implant mass 20 absorbs enough plasticizer to be sufficiently moldable, but not completely dissolved or softened so much as to yield a soapy liquid that is not moldable.

Plasticizer 22 is advantageously biocompatible such that it can be placed in a person without significant complications. In one embodiment, plasticizer 22 is selected from NMP, acetone, or an alcohol, such as ethanol. Plasticizer 22 can be the same as one of the chemicals used to make implant mass 20, or it can be a different solvent or softener.

In an alternative embodiment unshaped implant mass 20 is placed in a container and exposed to a gaseous plasticizer (not shown). Implant mass 20 absorbs the gaseous plasticizer and becomes moldable.

As shown in FIG. 2C, softened implant mass 20a is sufficiently moldable such that it can be forced into bone defect 26 of bone 24. When softened implant mass 20a is forced into bone defect 26 it deforms and takes the shape of bone defect 26, while causing little or no damage to bone 24 and adjacent tissue.

FIG. 2D shows shaped implant mass 20b, which has been molded to the shape of defect 26. Because implant mass 20b is in bone 24, body fluids in and/or surrounding bone 24 come into fluid contact with implant mass 20b. Plasticizer 22 is at least partially soluble in the body fluids of bone 24 and is eventually drawn out of implant mass 20b thereby causing the bone implant to harden. The polymer bonder, on the other hand, is preferably sufficiently insoluble in water in order to prevent the shaped implant mass 20b from further softening, rather than hardening, when wetted or hydrated with bodily fluid.

FIGS. 3A-3D illustrate an alternative process for forming a shaped implant from a softened unshaped implant mass 20a. An initially hard and unshaped implant mass 20 is conditioned using plasticizer 22 as described with reference to FIG. 2B to yield a softened (or moldable) implant mass 20a. Moldable implant mass 20a is then forced into a mold 28 to form a shaped implant mass 20b. Mold 28 can have any desired mold cavity (e.g. the shape of an extracted tooth root, a cylinder, or other regular or irregular shape).

As shown in FIG. 3B, a hardener 30 is added to shaped implant mass 20b in mold 28 using a syringe 32. Hardener 30 is a liquid selected to extract or neutralize the plasticizer 22 (FIG. 2B). In one embodiment, hardener 30 is a substances in which plasticizer 22 is soluble. Thus, hardener 30 draws plasticizer 22 out of shaped implant mass 20b thereby forming a hardened implant composition 20c, as shown in FIG. 3C. In an exemplary embodiment, hardener 30 is water. Finally, in FIG. 3D, hardened implant mass 20c is extracted from mold 28 and placed into a defect 26a within bone 24.

Mold 28 is usually formed to have the same shape as the bone defect that needs to be filled. Typically, using a mold is convenient when a negative impression of the defect can be easily made. For example, where the root of a tooth is extracted from a bone, the root can be used to make a mold of the tooth extraction site. In another example, a replacement bone or bone portion can be sculpted and then used to make a mold.

FIG. 4 illustrates another exemplary embodiment of a method of the present invention. FIG. 4A shows dried coated granules 34 in a container 36. In one embodiment, granules 34 are prepared using a fluid-bed machine as described above and allowed to dry. Because granules 34 are dry, they do not agglomerate to form an implant mass. Dry granules 34 are particularly convenient to store and ship.

As shown in FIGS. 4B and 4C, to use granules 34 in an implant, plasticizer 22 is added to granules 34 using syringe 38 and then stirred using spatula 40 for form an unshaped moldable mass of implant granules 34a.

FIG. 4D illustrates forming a shaped implant mass 34b from moldable implant mass 34a. Moldable implant granules 34a are placed in bone defect 42 of bone 44 using spatula 40. Moldable granules 34b adhere together to form a shaped implant mass 34b that conforms to the shape of bone defect 42. In one embodiment, body fluids in and/or surrounding bone 44 come into contact with shaped implant mass 34b and extract plasticizer 22 therefrom, thereby causing shaped implant mass 34b to harden.

In a similar embodiment, container 36 is a syringe, rather than a tray. In this embodiment, the granules and solvent are mixed in the syringe to form an unshaped implant mass. The softened implant mass can then be injected directly into a bone defect using the syringe, without the need to use a spatula 40. In one embodiment, the granules and/or the plasticizer can be prepackaged in the syringe such that the implant is ready for use by a practitioner. Alternatively the granules and/or the solvent can be mixed in the syringe just prior to use.

In an alternative embodiment moldable implant granules 34a described with reference to FIG. 4C can be used in a mold to make a shaped implant. As shown in FIG. 5A, moldable granules 34a are placed into a mold 46 using spatula 40. Moldable granules 34a conform to the shape of mold 40 to form a shaped implant mass 34b.

FIG. 5B illustrates a hardener 30 being added to the shaped implant mass 34b, using syringe 32. Hardener 30 extracts plasticizer 22 to cause the shaped implant mass 34b to harden and form hardened implant mass 34c as illustrated in FIG. 5C. In one embodiment, hardener 30 is water and plasticizer 22 is at least partially soluble in hardener 30. Finally, as shown in FIGS. 5C and 5D, hardened implant mass 34c is extracted from mold 46 and placed into bone defect 42 of bone 44.

In yet another embodiment, the methods described with reference to FIGS. 4 and 5 can be carried out using coated granules that are not dry. In this embodiment, the coated granules already contain plasticizer and are therefore moldable. Coated granules suitable for use in this embodiment can be produced using a fluidized bed machine. In this embodiment, a plasticizer is used to make the coated granules in the fluidized bed machine. However, instead of allowing the granules to dry, the moldable granules are used to form a shaped implant mass. Since the granules never become dry and are thus initially moldable, there is no need to add additional plasticizer. Alternatively, additional plasticizer can be added and/or a portion of the original plasticizer removed to yield a moldable mass having a desired rheology. The implant mass can be shaped by placing the moldable granules directly in a bone defect or by first placing them in a mold.

In each method described above, the implant mass is eventually inserted into a living organism. The implant can be administered to a patient by any technique known for insertion of implants into body tissue. Typically, the bone implant is inserted into an incision formed in the patient either under the skin, in the skeletal muscle or through a laparoscopic device for insertion of implants into internal organs or tissues. The incision is closed such as by cauterization or suture. If the implant is biodegradable, the implant is allowed to remain in-situ until the body decomposes it. Generally, the medical techniques for implantation of foreign materials into the body are known to skilled surgeons and are practiced following the wisdom and judgment of such medical practitioners.

The present invention is further exemplified in the following examples, which are offered by way of illustration and are not intended to limit the invention in any manner.

EXAMPLE 1

β-TCP granules were coated with a PLGA layer in a fluidized bed machine and allowed to dry. The coated β-TCP granules were then exposed to a vapor of NMP at about 100° C. for about 5 minutes. NMP molecules were absorbed into the PLGA coating partially dissolving the PLGA and making the coated granules moldable and slightly sticky. A mold having the shape of a tooth root was filled with about 0.5 grams of sticky, moldable granules. The mold was then immersed into a water bath for about 5 minutes. The implant mass was sufficiently hardened such that it could be extracted from the mold and implanted in the tooth root extraction site without substantially deforming the implant.

EXAMPLE 2

β-TCP granules were coated with a PLGA layer using a fluidized bed technique. A plasticizer comprising ten drops of NMP (alternatively 5 drops of acetone were added to 0.5 grams of coated β-TCP granules and homogenously mixed in a Petri dish with a spatula until the plasticizer was dispersed. The absorption of the plasticizer made granules slightly sticky. The granules were then placed into a periodontic defect model using a spatula to completely fill the defect. The granules were rinsed with 100 ml of deionized water to simulate contact with a body fluid. The water treatment extracted the NMP (or acetone) thereby provoking the solidification of the implant.

EXAMPLE 3

β-TCP granules having a diameter from 500 μm to 100 μm were coated with PLGA in a 6% by weight of polymer in a solution of acetone using a fluidized bed technique. At the end of the coating procedure, no drying step was performed. Once the air flow in the fluidized bed was stopped, the granules began to stick together upon contact. The granules were ready to be used to directly fill a skeletal bone defect after γ-radiation sterilization. Body fluids in and around the skeletal bone extract the acetone to provide a mechanically stable implant.

EXAMPLE 4

β-TCP granules coated with PLGA were poured into a cylindrical mold. After a brief heating at about 70° C., the granules stuck together to form a mechanically stable unshaped implant mass. The implant mass was tested and withstood a vertical load of 30N without significant deformation.

The unshaped implant mass was then exposed to boiling acetone for 2 minutes. The 30N vertical load was immediately applied to the implant mass and a vertical deformation of about 40% was observed.

Finally, a second implant mass identical to the first implant was treated for 2 minutes in boiling acetone. The implant mass was then immersed in water for 15 hours to allow the absorbed acetone to diffuse out of the polymer layer. A 30N vertical load was applied to the implant mass and a deformation of about 7% was observed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A moldable implant mass composition for use in repairing a bone defect in a living organism, comprising:
   a plurality of biocompatible synthetic non-polymeric granules, said granules having an equivalent diameter of about 100 μm to about 4,000 μm;
   a biocompatible polymer coating at least a portion of the implant mass, the implant mass comprising a composite matrix of the granules bound to each other by adhesion between the biocompatible polymer disposed on adjacent granules, and macropores between adjacent granules, so as to form an implant mass comprising a plurality of distinct granules coated with said biocompatible polymer, said biocompatible polymer comprising about 4% to about 20% of the total weight of the implant mass; and
   a plasticizer in said implant mass in an amount sufficient to condition at least a portion of said biocompatible polymer so that said implant mass is plastically deformable into a desired shape and then hardenable upon removal of at least a portion of said plasticizer from said implant mass, and so that adhesion between the biocompatible polymer coating disposed on adjacent granules is promoted.

2. A moldable implant mass composition as defined in claim 1, wherein the granules comprise at least one material selected from the group consisting of biocompatible ceramics, and biocompatible glasses.

3. A moldable implant mass composition as defined in claim 1, wherein the granules comprise at least one material selected from the group consisting of silicon oxide, calcium sulphate, and calcium phosphate.

4. A moldable implant mass composition as defined in claim 1, wherein the granules comprise at least one material selected from the group consisting of monocalcium phosphate monohydrate, monocalcium phosphate anhydrous, dicalcium phosphate dihydrate, dicalcium phosphate anhydrous, tetracalcium phosphate, calcium orthophosphate phosphate, calcium pyrophosphate, α-tricalcium phosphate, β-tricalcium phosphate, hydroxyapatite, carbonate hydroxyapatite, apatite, and bioglass.

5. A moldable implant mass composition as defined in claim 1, wherein the granules are biodegradable.

6. A moldable implant mass composition as in defined claim 1, wherein said biocompatible polymer is biodegradable.

7. A moldable implant mass composition as defined in claim 1, wherein said biocompatible polymer comprises at least one polymer selected from the group consisting of poly (a-hydroxyesters), poly(orthoesters), poly(ether esters), polyanhydrides, poly(phosphazenes), poly(propylene fumarates), poly(ester amides), poly(ethylene fumarates), poly (amino acids), polysaccharides, polypeptides, poly(hydroxy butyrates), poly(hydroxy valerates), polyurethanes, poly (malic acid), polylactides, polyglycolides, poly (lactide-co-glycolide), polycaprolactones, poly(glycolide-co-trimethylene carbonates), and polydioxanones.

8. A moldable implant mass composition as defined in claim 1, wherein the biocompatible polymer comprises poly (lactide-co-glycolide).

9. A moldable implant mass composition as in claim 1, wherein said plasticizer is selected from the group consisting of n-methyl-2-pyrrolidone, acetone, ethyl lactate, ethyl acetate, ethyl formiate, acetyltributylcitrate, triethyl citrate, lactic acid, citric acid tetrahydrofuran, toluene, alcohol and carbon dioxide.

10. A moldable implant mass composition as defined in claim 1, further comprising a biologically active substance.

11. A moldable implant mass composition as defined in claim 1, wherein said plasticizer is extractable from said implant mass when contacted with a hardener.

12. A moldable implant mass composition as defined in claim 11, wherein said hardener comprises water or a body fluid.

13. A moldable implant mass composition as defined in claim 1, in combination with a syringe that is capable of injecting the moldable implant composition into a bone defect.

14. The moldable implant mass composition as defined in claim 1, wherein the granules are regularly-shaped, regularly-sized, or spherical.

15. The moldable implant mass composition as defined in claim 14, wherein the granules have an equivalent diameter of about 100 μm to about 4,000 μm and the polymer coating has a thickness of about 1 μm to about 300 μm.

16. The moldable implant mass composition as defined in claim 14, wherein the granules have an equivalent diameter of about 500 μm to about 1,500 μm, and the polymer coating has a thickness of about 5 μm to about 30 μm.

17. The moldable implant mass composition as claimed in claim 1, wherein the implant composition in claim 1, wherein the implant composition does not contain bone particles.

18. The moldable implant mass composition as defined in claim 1, wherein the macropores have an average diameter of about greater than 10 μm to about 2000 μm.

19. The moldable implant mass composition as defined in claim 18, wherein the macropores have an average diameter of about 100 μm to about 500 μm.

20. The moldable implant mass composition is defined in claim 1, wherein the granules or biocompatible polymer comprise micropores.

21. The moldable implant mass composition of claim 20, wherein the biocompatible polymer comprises polylactide-co-glycolide, and the plasticizer comprises n-methyl-2-pyrrolidone, acetone, or an alcohol.

22. The moldable implant mass composition as defined in claim 1, wherein the granules comprise calcium phosphate.

23. The moldable implant mass composition of claim 22, wherein the calcium phosphate comprises β-tricalciumphosphate or hydroxyapatite.

24. The moldable implant mass composition of claim 1, wherein the granules comprise regularly-shaped spherical particles having a homogenous coating of the biocompatible polymer.

25. A composite implant mass comprising:
a structural component, the structural component comprising a plurality of biocompatible synthetic non-polymeric granules, the granules being regularly-sized, regularly shaped, or spherical, and the granules having an equivalent diameter of about 100 μm to about 4,000 μm;
a biocompatible polymer on at least a portion of each of the granules; and
a plasticizer in an amount sufficient to condition at least a portion of the biocompatible polymer so that the granules of the implant mass are bound to each other by adhesion between the biocompatible polymer disposed on adjacent granules, and the implant mass is plastically deformable.

26. The implant mass of claim 25, wherein the biocompatible polymer comprises 4% to 20% of the total weight of the implant mass.

27. The implant mass of claim 25, wherein the granules have an equivalent diameter of about 500 μm to about 1,500 μm.

28. The implant mass of claim 25, wherein the granules have a coating of the polymer and are distinct from one another.

29. The implant mass of claim 28, wherein the coating has a thickness of about 1 μm to about 30 μm.

30. The implant mass of claim 25, wherein the coating has a thickness of about 5 μm to about 30 μm.

31. A composite matrix comprising:
a structural matrix, the structural matrix comprising a plurality of biocompatible synthetic non-polymeric granules bound to each other, at least in part, by adhesion between a biocompatible polymer coating formed on each of the adjacent granules, wherein adhesion between the biocompatible coating formed on each of the adjacent granules is promoted by a plasticizer; and
an open porous region comprising macropores between adjacent coated granules;
wherein the structural matrix does not contain any bone particles.

32. The composite matrix of claim 31, further comprising a membrane on a surface of said composite matrix.

33. The composite matrix of claim 31, wherein the open porous region is filled with air or gas.

34. The composite matrix of claim 31, wherein the open porous region is filled with a liquid, solid particles, or a gel.

35. The composite matrix of claim 31, wherein the biocompatible polymer comprises 4% to 20% of the total weight of the composite.

36. The composite matrix of claim 31, wherein the granules are regularly-sized, regularly-shaped, or spherical.

37. The composite matrix of claim 31, wherein the macropores have an average diameter of about greater than 10 μm to about 2000 μm.

38. The composite matrix of claim 37, wherein the macropores have an average diameter of about 100 μm to about 500 μm.

* * * * *